(12) United States Patent
Marzorati et al.

(10) Patent No.: US 8,703,479 B2
(45) Date of Patent: Apr. 22, 2014

(54) TECHNOLOGY AND METHOD TO STUDY MICROBIAL GROWTH AND ADHESION TO HOST-RELATED SURFACES AND THE HOST-MICROBIOTA INTERACTION

(71) Applicant: Universiteit Gent, Ghent (BE)

(72) Inventors: Massimo Marzorati, Ghent (BE); Sam Possemiers, Ghent (BE); Pieter Van Den Abbeele, Ghent (BE); Tom Van De Wiele, Ghent (BE); Barbara Vanhoecke, Ghent (BE); Willy Verstraete, Ghent (BE)

(73) Assignee: Universiteit Gent, Ghent (BE)

( * ) Notice: Subject to any disclaimer, the term of this patent is extended or adjusted under 35 U.S.C. 154(b) by 0 days.

(21) Appl. No.: 13/861,590

(22) Filed: Apr. 12, 2013

(65) Prior Publication Data

US 2013/0203161 A1 Aug. 8, 2013

Related U.S. Application Data

(62) Division of application No. 13/264,018, filed as application No. PCT/EP2010/002286 on Apr. 14, 2010.

(30) Foreign Application Priority Data

Apr. 14, 2009 (GB) .................................. 0906236.5

(51) Int. Cl.
*C12M 1/12* (2006.01)
(52) U.S. Cl.
USPC .................................................... 435/297.1

(58) Field of Classification Search
USPC .......... 435/297, 289.1–297.1, 1.1, 1.2, 284.1, 435/299.1, 305.2
See application file for complete search history.

(56) References Cited

U.S. PATENT DOCUMENTS

| | | | |
|---|---|---|---|
| 5,525,305 A | 6/1996 | Minekus et al. | |
| 5,888,807 A | 3/1999 | Paisson et al. | |
| 6,759,245 B1 * | 7/2004 | Toner et al. | 435/401 |
| 7,534,610 B1 * | 5/2009 | Kotov et al. | 435/402 |
| 2004/0101906 A1 | 5/2004 | Lacroix et al. | |
| 2005/0186633 A9 | 8/2005 | Lacroix et al. | |

FOREIGN PATENT DOCUMENTS

| | | |
|---|---|---|
| EP | 2130905 A1 | 12/2009 |
| WO | 9409895 A1 | 5/1994 |

OTHER PUBLICATIONS

Ukena et al. The host response to the probiotic *E. coli* strain Nissle 1917: Specific up-regulation of the proinflammatory chemokine MCP-I. (Dec. 13, 2005). BMC Medical Genetics 6:43.*

Sue Hyung Choi, Masaki Nishikawa, Akiyoshi Sakoda, Yasuyuki Sakai. Feasibility of a simple double-layered coculture system incorporating metabolic processes of the intestine and liver tissue: application to the analysis of benzo[a]pyrene toxicity. (2004). Toxicology in Vitro. 18, 393-402.*

(Continued)

*Primary Examiner* — Sean E Conley
*Assistant Examiner* — Donald Spamer
(74) *Attorney, Agent, or Firm* — Dinsmore & Shohl LLP

(57) ABSTRACT

A method is provided for co-culturing viable cells and microorganisms for at least 48 hours in which an adhesion module is provided including a basal compartment and a luminal compartment separated by a semi-permeable membrane, and a continuous or semi-continuous flow of fresh medium is applied to the basal compartment.

11 Claims, 5 Drawing Sheets

(56) References Cited

OTHER PUBLICATIONS

Human enterocyte (Caco—2) migration is modulated in vitro by extracellular matrix composition and epidermal growth factor. Basson et al. Journal of Clinical Investigation. 1992. 90(1):15-23.*

Atuma et al., "The adherent gastrointestinal mucus gel layer: thickness and physical state in vivo", American Journal Physio Gastrointest Liver Physiol 280, pp. G922-G929, 2001.

Laube et al., "Establishment of a novel in vitro system for studying the interaction of xenobiotic metabolism of liver and intestinal microflora", Arch Toxicol 74, pp. 379-387, 2000.

Linden et al., "Improved in vitro Model Systems for Gastrointestinal Infection by Choice of Cell Line, pH Microaerobic Conditions, and Optimization of Culture Conditions", Helicobacter 12 ISSN 1523-5378, pp. 341-353, 2007.

MacFarlane et al., Applied and Environmental Microbiology, vol. 71, No. 11, pp. 7483-7492, Nov. 2005.

MacFarlane et al., "Microbial biofilms in the human gastrointestinal tract", Journal of Applied Microbiology 102, ISSN 1364-5072, pp. 1187-1196, 2007.

MacFarlane et al., "Models for intestinal fermentation: association between food components, delivery systems, bioavailability and functional interactions in the gut", Current Opinion in Biotechnology 18, pp. 156-162, 2007.

Molly et al., "Validation of the Simulator of the Human Intestinal Microbial Ecosystem (SHIME) Reactor Using Microorganism-associated Activities", Microbial Ecology in Health and Disease vol. 7, pp. 191-200, Jan. 1994.

Nollevaux et al., "Development of a serum-free co-culture of human intestinal epithelium cell-lines (Caco-2/HT29-5M21)", BioMed Central, pp. 1-11, 2006.

Parlesak et al., "Modulation of Cytokine Release by Differentiated CACO-2 Cells in a Compartmentalized Coculture Model with Mononuclear Leucocytes and Nonpathogenic Bacteria", Scandinavian Journal of Immunology 60, pp. 477-485, 2004.

Probert et al., "Development of a fermentation system to model sessile bacterial populations in the human colon", Biofilms 1, pp. 13-19, 2004.

International Preliminary Report on Patentability for Application PCT/EP2010/002286 dated Oct. 27, 2011.

Search Report for PCT/EP2010/002286 dated Oct. 13, 2010.

Elections/Restriction pertaining to U.S. Appl. No. 13/264,018 dated Aug. 3, 2012.

Office Action pertaining to U.S. Appl. No. 13/264,018 dated Sep. 20, 2012.

Final Rejection pertaining to U.S. Appl. No. 13/264,018 dated Jan. 15, 2013.

Basson et al. "Human enterocyte (Caco-2) migration is modulated in vitro by extracellular matrix composition and epidermal growth factor", Journal of Clinical Investigation 90(1), pp. 15-23, 1992.

* cited by examiner

PRIOR ART

TECHNOLOGY AND METHOD TO STUDY MICROBIAL GROWTH AND ADHESION TO HOST-RELATED SURFACES AND THE HOST-MICROBIOTA INTERACTION

CROSS REFERENCE TO RELATED APPLICATIONS

This application is a divisional of U.S. patent application Ser. No. 13/264,018 filed Nov. 9, 2011, entitled TECHNOLOGY AND METHOD TO STUDY MICROBIAL GROWTH AND ADHESION TO HOST-RELATED SURFACES AND THE HOST-MICROBIOTA INTERACTIONS, which application is a national phase entry of PCT/EP2010/002286 filed Apr. 14, 2010, which claims priority to Great Britain Patent Application No. 0906236.5 filed Apr. 14, 2009. The entire contents of said application is hereby incorporated by reference.

The present invention relates to in vitro models that allow growth, stabilization and study of microbial communities that adhere to and colonize host-related surfaces and that mimic transport of chemical compounds across epithelial surfaces and that allows the host-microbiota adaption and signal exchange.

BACKGROUND OF THE INVENTION

The human body hosts a tremendously diverse microbial community on external and internal host surfaces such as the skin, respiratory tract, mouth, gastrointestinal tract, reproductive tract, urinary tract and eyes. The total number of microbial cells ($10^{14}$) exceeds the number of host cells ($10^{13}$) with an order of magnitude and comprises many thousands of species. Their enormous enzymatic diversity, their capacity to trigger host immunological responses and the possibility of modulating physiological processes within the host that are involved in the etiology of cancer, obesity, or cardiovascular diseases, makes these host-associated microorganisms a confounding factor in the general health-status of an individual.

More in particular, the gastrointestinal tract, which is still an environment external to the host's body, is a site where the microbial involvement in host processes is highly significant. Up to now, many studies have targeted the microbial community in the gut lumen by investigating their fermentation activity, metabolic potencies and changes in community composition due to certain treatments. However, specific microbe-host interactions often depend on the ability of microorganisms to adhere to the gut surface. Previous studies employed cell culture experiments such as Caco-2, T84, HT29 etc. to investigate the specific adhesion of probiotic or pathogenic microorganisms to epithelial cells. Yet, for reasons of cytotoxicity, cell cultures are very sensitive to co-incubation with mixed microbial slurries, thus limiting the experimental time to 2 hours maximally. Moreover, the growth of cell cultures is time-consuming and it is not possible to perform high-throughput screenings to evaluate many bacteria or components at the same time.

It has been proposed that the structure and composition of the gastrointestinal ecosystem reflects a natural selection at both microbial and host levels. Such ecosystem requires a series of evolved, nested equilibria to achieve the overall homeostasis, in analogy with the Evolutionary Stable Strategy theory. Host-derived signals and microbial-derived signals may be either unlinked or linked. Linked signals imply a selective pressure based on and favoring co-evolution (Blaser and Kirschner, 2007, Nature, 449: 843-849). The above mentioned natural selection primarily occurs along mucosal surfaces by a host-microbiota cross-talk that leads to the modulation of the host immunity.

Specific immunological signalling pathways may be triggered upon recognition by the host of microbial cell wall patterns. Microorganisms have a wide variety of MAMPs (Microbial Associated Membrane Patterns), which can be recognized by specific host receptors on epithelial cells. An example of this recognition process is the family of Toll Like Receptors (TLR), which recognize specific microbial adhesins such as lipopolysaccharides (LPS), lipoteichoic acids, fimbriae, pili etc. However, in the intestinal epithelium, where the interaction between the host and the endogenous microbiota is the highest, TLR can be downregulated. Prior to microbial invasion of epithelial cells, microorganisms need to reach the epithelium. However, there is no direct contact between luminal bacteria and the epithelial surfaces. The actual surface that bacteria encounter when approaching the host epithelium, is the mucus layer covering the epithelium. The study of the microbial ability to adhere to the intestinal mucus layer is therefore an important prerequisite when assessing a microorganism's ability to interact with the host. Although it is possible to trigger mucus production in for example HT29 (Novellvaux et al., 2006) as well as MKN1, MKN7 and MNK45 cell-lines (Linden et al., 2007), it is not possible to monitor colonization and persistence of mixed microbial communities on these cells for reasons of cytotoxicity. In vitro models allowing the study of microbial mucus colonization over a longer time-frame are therefore much needed.

The main constituents of mucus are mucins, which are usually present at a concentration ranging between 2% to 10% (w/v). These are glycoproteins containing high proportions of carbohydrates—usually between 70% to 85% (w/w). The mucins are unusual glycoproteins in that most of the carbohydrate side-chains are linked to the protein at serine and threonine residues via an oxygen atom (i.e., they are "O-glycosylated"), although N-glycosylation also occurs. The structure of a typical mucin molecule consists of a protein to which carbohydrate side-chains are linked by O-glycosylation and/or N-glycosylation. The protein backbone consists of several thousand amino-acid residues (in the case of MUC2, a major type of mucin found in the gastro-intestinal system (GIT), the number of amino acids is 5,179) and contains regions with many oligosaccharide side-chains and other regions without such side-chains. The oligosaccharide-rich regions are resistant to proteases, whereas the other regions are protease-sensitive. The oligosaccharide-containing regions of the protein are rich in serine, threonine and proline. The side-chains usually consist of two to twelve residues from a restricted range of sugars—usually galactose, fucose, N-acetylglucosamine, N-acetylgalactosamine, mannose and sialic acids.

The protein backbones of the various mucins produced are encoded by a large family of MUC genes. Which of these genes are expressed depends on the particular body site. Hence, MUC2 is the main type of mucin protein produced in the intestinal tract whereas the expression of six MUC genes has been detected in the cervix with different patterns of expression at different phases of the menstrual cycle. In the oral cavity, two well-known secreted mucins, mucus glycoprotein 1 (MG1) and mucus glycoprotein 2 (MG2), have been identified. High-molecular-weight MG1 consists mainly of the MUC5B gene product (Nielsen et al., 1997), whereas the low-molecular-weight MG2 is a product of the MUC7 gene (Bobek et al., 1993). However, only a few investigators have reported expression of membrane-associated mucins in the human oral cavity. Sengupta et al. (2001) reported that MUC1 was expressed in the ducts of the minor salivary. Liu et al. (2002) showed that MUC1 and MUC4 but not MUC3 and MUC13 were expressed in the human parotid and submandibular glands. Recently, it has been shown that cultivated stratified human oral mucosal epithelial sheets express the transcripts for the membrane-associated mucins, MUC1, MUC4, and MUC16 but not MUC3, MUC12, MUC13, MUC15, and MUC17 (Hori et al., 2007; Hon et al., 2008).

Differences also exist with regard to the glycosylation patterns of a particular type of mucin protein—hence the composition of the carbohydrate side-chains of a mucin with a MUC 1 protein backbone will be different in the respiratory and intestinal tracts.

Besides mucus adhesion, some bacteria can invade the mucus layer and utilize mucin as Carbon, Nitrogen and energy source. Mucin polymers need to be hydrolyzed, prior to the assimilation of mucin oligomers, mucin monomers and amino acids. The structural complexity of mucin polymers entails that the complete degradation of them by a single microbial species is unlikely. Such degradation requires the production of a whole range of enzymes in a certain order because regions of the molecule only become accessible once others have been removed. This is more readily accomplished by microbial consortia rather than by individual species. The range of enzymes needed to achieve complete degradation of mucin is shown in Table 1.

TABLE 1

Enzymes required for complete mucin degradation

| Type of enzyme | Role in mucin degradation |
| --- | --- |
| Sulphatases | Removal of terminal sulphate residues, thereby exposing underlying sugars rendering them more susceptible to the action of glycosidases. |
| Sialidase (neuraminidases) | Removal of terminal sialic acid residues: this exposes underlying sugars to the action of glycosidases: the sialic acid itself can be further degraded by acetylneuraminate pyruvate lyase to N-acetylmannosamine which can be used as Carbon and energy source by some bacteria. |
| Exoglycosidases | Cleave sugars from side chains (e.g. β-D galactosidase, N-acetyl-β-D galactosaminidase, a-fucosidase, N-acetyl-β-D glucosaminidase). |
| Endoglycosidases | Cleave entire side-chain from the peptide backbone or attack the side-chain at sites other than the terminal residue - this may occur before or after the side-chain has been cleaved from the protein. |
| Peptidases/ proteases | Cleave at non-glycosylated regions: degrade protein backbone after side-chains have been removed. |

The ability to degrade mucin, entirely or partially, has been detected in microbes or microbial consortia inhabiting all mucosal sites of the body. The removal of carbohydrates and other components from the glycoprotein compromises the protective function in the gut, especially when the rate of mucus breakdown exceeds the rate of mucus production. The composition and metabolic activity of mucosal microbial communities is quite different from the luminal microbial communities in the gut. Given their ecological significance regarding gut microbiota composition and their putative role in inflammatory bowel disease such as ulcerative colitis, it is crucial to understand the colonization, composition and metabolic activity of the gut mucosal microbial population.

Once gut microorganisms can adhere to the mucosa, they have the chance of forming a biofilm on the mucosa within the timeframe that the host epithelium renews its mucus layer. Biofilms are considered to reflect the most common steady-state for bacterial growth (Costerton, 1995) with the gut microbial biofilm constituting a driving factor in the establishment and maintenance of the spatially diversified microbial community (Hooper and Gordon, 2001). A special feature of mucosal biofilms is the presence of oxygen at the base, due to diffusion from the host blood stream across the epithelium. Luminal oxygen concentrations in the colon can even rise to 30 mm Hg. This would compromise the colonization and growth of strict anaerobes such as sessile Fusobacteria which are found to have an important "bridging" function within biofilms, forming co-aggregation/co-adhesion bridges between early colonizers and late colonizers and thus contributing towards biofilm establishment and accumulation (Kolenbrander et al., 2000). Yet, the growth of Fusobacteria in the mucus biofilm is tenable because of their local association with aerobes and facultative anaerobes, which locally deplete the mucus layer of oxygen. The presence of oxygen in the mucus layer also allows the production of reactive oxygen species such as for example $O_2-$, $H_2O_2$ and OH from bacterial origin. For example, Enterococcus faecalis has been shown to form hydroxyl radicals by aromatic hydroxylation, thus being able to elicit oxidative stress towards the epithelium (Huycke and Moore, 2002).

Different in vitro approaches have been used to evaluate the influence of substances and organisms on the gastrointestinal system and its flora including both batch and continuous culture systems.

Batch Type Fermentors

Short term batch culture systems allow a rapid screening and a flexible design to assess for instance the interindividual variability. However, in this simplified environment, the control of changing conditions is not possible and only short term experiments can be conducted.

Single-Stage Continuous Fermentors

Single-stage continuous fermentors offer a better model for specific regions of the GI tract under controlled conditions. Nevertheless, stability of the microbial community under long term studies is not always possible.

The Reading Simulator

The Reading simulator (Macfarlane and Macfarlane, 2007) simulates the gut using a 3 stage continuous culture with three glass vessels (220 ml, 320 ml and 320 ml) and different pH in each vessel (5.8, 6.2, and 6.8), mimicking the human proximal, transverse, and distal colon, respectively. Each vessel is inoculated with 100 ml of 20% (w/v) of human feces. The system is run for 14 days in order to achieve a steady-state condition in the vessels, then for 3 weeks to test a specific compound and finally, for a washout period (2 weeks) to determine how long the changes induced by the test substance can still be measured in the absence of the substrate itself.

The EnteroMix Colon Simulator

The EnteroMix model has four parallel units each comprising four glass vessels, allowing four simulations to be run simultaneously using the same fecal inoculum (Makivuokko et al., 2006). EnteroMix model vessels 1, 2, 3, and 4 have small working volumes (6, 8, 10, and 12 ml, respectively). The pH levels are controlled. The simulation begins with three hours of incubation of 10 ml of the fecal inoculum and then 3 ml of fresh simulator medium with (three test channels) or without (one control channel) test substance is pumped to the first vessel. The medium is fermented in the first vessel for three hours, after which 3 ml of the fermented medium are transferred to the second vessel, and 3 ml of fresh medium are pumped to the first vessel. The fermentation lasts for 48 hours, after which samples are collected from each vessel and the simulation is terminated.

In the two latter systems the upper part of the GI tract (stomach and small intestine) is completely absent. Moreover, in the EnteroMix colon simulator, the volumes are small when compared with the in vivo situation, there is no stabilization of the microbial community and only short experiments can be performed.

In Vitro Gastrointestinal System Models (GIT)

Currently there are two complete in vitro GIT models available in which studies can be performed and labor, time and costs are reduced when compared with in vivo studies, without ethical constraints. In these two systems, the kinetics of the gut are simulated by controlling the concentrations of gastric, small intestinal and pancreatic enzymes, bile, pH, temperature, feed composition, transit time in the GIT and the anaerobic environment with physiological relevance.

TIM 1 and 2 (TNO Intestinal Model)

The first in vitro GIT model is TNO's gastrointestinal model (TIM). This model actually comprises two complementary parts; the systems 1 and 2 introduced by Minekus et al. in 1995 and 1999 (US55255305 and Minekus et al., 1999) and WO1994009895. The TIM 1 system contains four computer-controlled chambers simulating the conditions of stomach, duodenum, jejunum and ileum. The TIM 2 system consists of four glass modules mimicking the proximal colon of monogastric animals. In these dynamic models fluid transportation from vessel to vessel happens via peristaltic valve-pumps and there is constant, although passive, absorption of water and fermentation products through dialysis membranes. For the simulation of intestinal absorption TIM 1 has two integrated 5 kDa dialysis membranes, next to jejunal and ileal modules. TIM 2 has one hollow-fiber membrane (molecular mass cut-off value 50 kDa) in the luminal part en of the system. The pH-values are monitored in each compartment. In a TIM 2 simulation the model is inoculated with 200 ml of fecal inoculum. Microbiota are allowed to adapt to the conditions for 16 hours, however there is no long-term stabilization of the microbial community and the volumes in the different chambers are small when compared with in vivo situations.

The Simulator of the Human Intestinal Microbial Ecosystem (SHIME)

The second in vitro GIT model is the SHIME. The conventional SHIME is a dynamic model of the human gut comprising 5 compartments respectively simulating the stomach, small intestine and ascending, transverse and descending colon. The stomach and small intestine compartments mimic the enzymatic and physicochemical environment by controlling pH and residence time and the dosing of a proper nutritional medium, enzymes and bile salts. By controlling the pH, redox potential and residence times, the different colon compartments each harbor a microbial community that corresponds to that of the in vivo situation in terms of metabolic activity and community composition. In this model a typical stabilization period of three weeks and a basal period of two weeks are followed by treatment and wash-out periods.

Biofilm Simulation Model (Lacroix, Switzerland)

All the models presented until now do not take into account an important aspect in the GI tract: adhesion of microorganisms to the mucus layer, biofilm formation and its potential role on the host physiology and structuring of the microbial community and on cross-talk. Patent applications US2005186633 and US20040101906 from Lacroix et al. (2005) addressed the issue of the biofilm formation in the GI tract. They claimed a system utilizing cell immobilization in anaerobic continuous-flow cultures for modeling GI system. Microbes from fresh fecal samples are immobilized in a mixed gel of gellan and xanthan on beads and are then introduced in a single or multi-stage chemostat (continuous culture system) simulating the biofilm typically forming in the GI tract. This system allows the microorganisms to adhere. At the same time, however, it lacks the key point that specifically characterizes the mucosal biofilm namely, the anaerobic conditions prevailing at the top of the biofilm and microaerophilic conditions prevailing at the base of the biofilm.

Probert and Gibson (2004) provided a similar device with a framework of mucin beads encased within a dialysis membrane. The system is inoculated with fecal samples and water and metabolites are removed by osmosis using a solution of polyethylene glycol.

Finally, Macfarlane et al. (2005) developed a two-stage continuous culture system, simulating the proximal and distal colon, and used sterile porcine mucin gels in small glass tubes to determine how intestinal bacteria colonize and degrade mucus. These tubes can be placed in a fermentor simulating a specific area of the GI tract and removed over a period of 48 h for further analyses of on the biofilm.

These systems allow the microorganisms to adhere but do not offer the opportunity of studying the gut biofilm formation (Lebeer et al., 2007) and the host-microbial interaction under continuous simulated conditions.

Simulation of the Host-Bacteria Interaction

None of the aforementioned models simulating the GI tract has an adequate device to study the mechanisms of bacterial adhesion in response to the host signals and the reciprocal cross-talk. Previous studies use either germ-free animals (mainly rodents and, more recently, zebrafishes—Cheesman and Guillemin, 2007) or cell culture experiments (mainly Caco-2 or HT29 cells).

Animal studies demonstrated that vertebrates possess a broad scala of preserved interactions with the microbes with which they co-evolve (Cheesman and Guillemin, 2007) in particular when maintaining gut epithelial homeostasis, however, mechanistic studies are not always possible.

The in vitro use of cell lines can be limited by the fact that these cells do not produce a mucus layer (Caco-2 cells) or by the fact that pure microbial cultures or only a mix of few strains can be tested, for reasons of cytotoxicity. Cell cultures are very sensitive to co-incubation with mixed microbial slurries, thus limiting the incubation time and the adaptation of the host and the microbial metabolism.

One interesting model has been developed by Laube et al. (2000) to simulate the sequential metabolism of chemicals by the liver and the intestinal microbiota. Here, in a double chamber system, hepatocytes are cultivated as a monolayer on a membrane while, in the anaerobic compartment, the fecal microbiota are present in suspension. The exchange of metabolites can take place across the permeable membrane.

Another study has been conducted by Parlesak et al. (2004), investigating the interaction between human mononuclear leucocytes and enterocytes during challenge with a single bacterial species using compartmentalized transwell cell culture systems.

The transwell cell culture system has also been used by Linden et al. (2007), in which human gastrointestinal epithelial cell lines (e.g. MKN1, MKN7, Caco-2, . . . ) were grown on the apical side of a transwell and subsequently cocultured with different microbial strains.

Although the above described systems are very useful for short-term experiments, they are generally not suited to study the complex properties of the intestinal microflora over long-term studies, due to the cytotoxicity of the microbial cells towards the human cell layer.

In Vitro Model of the Present Invention

An in vitro test that does not represent the actual in vivo complexity will be unreliable when the results are extrapolated to an in vivo GIT situation (Pedersen and Tannock, 1989). Mucosal bacterial communities in the GI tract are difficult to study in vivo and biopsies are usually obtained from diseased individuals. Consequently, the data available may not provide a true indication of a normal mucosal diversity (Macfarlane and Dillon, 2007). Furthermore, an adequate device to study the mechanisms of bacterial adhesion in response to the host signals and their reciprocal cross-talks is not yet available.

Thus, there is a need for in vitro models that
reflect the in vivo GIT situation,
mimic the relevant environmental conditions of a mucosal layer,
can be adapted to a continuous system
allow the study of the adherence, colonization, composition and metabolic activity of the mucosal microbial population over a longer time-frame,
allow the formation of a mucosal biofilm with specific (in particular anaerobic or aerobic) conditions prevailing at the top of the biofilm and microaerophilic conditions prevailing at the base of the biofilm,
provide the possibility to perform experiments both with mono-cultures and with mixed and hence more relevant microbial communities, and/or
allow to evaluate the host-microbiota interaction and the consequent reciprocal adaptation.

The present invention describes different models to study microbial adhesion to mucosal surfaces. In particular the models of the present invention comprise 2 compartments separated by a semi-permeable membrane. Said membrane, on the luminal side being coated with an artificial mucus layer to which microorganisms applied in the luminal compartment are allowed to adhere. The use of said artificial mucus layers is advantageous compared to the use of mucus layers formed by epithelial cells, since direct interaction and as such also cytotoxicity between the microorganisms and the epithelial cells is prevented, allowing long-term analyses. Nevertheless, epithelial cells and/or other cell types can be grown in the basal compartment of the module and secretion products of these cells as well as of the microorganisms are allowed to diffuse through the membrane and artificial mucus layer in both directions. Furthermore, the use of two separate compartments allows the establishment of different oxygen pressures on both sides of the membrane. By regulation of the oxygen pressure in the individual compartments, optimal conditions for the aerobic epithelial cells in the basal compartment as well as for the anaerobic microorganism in the luminal compartment can be established. As will become evident from the examples hereinafter, the oxygen gradient across the semi-permeable membrane results in microaerophilic conditions at the luminal side of the artificial mucus layer that closely mimics the corresponding in vivo situation for the adhesion of microorganisms to said layer. Finally, the models allow an establishment of shear stress in the compartment containing the microorganisms, which is very important to mimic the in vivo situation. The combination of these features clearly distinguishes the model of the present invention from the models described in the prior art and provides a novel gastrointestinal tract model that closely mimics the corresponding in vivo situation.

SUMMARY OF THE INVENTION

The present invention relates to an adhesion module that can be used in an in vitro GIT model, comprising 2 compartments separated by a semi-permeable membrane; said membrane having an artificial mucus layer applied on its luminal site; and said module being characterized by anaerobic conditions at its luminal side and aerobic conditions at its basal side. Said mucus layer comprises at least one type of mucin and the thickness of the layer ranges between 1-1000 µm. The aerobic conditions in the basal compartment of the module can comprise an oxygen delivery at the basal side of the mucus layer ranging between 1 and 150 mmHg, in particular between 1 and 45 mmHg partial pressure.

The semi-permeable membrane allows the transport of components between 0-100000 Da, in particular between 0-10000 Da. The material of the semi-permeable membrane is polycarbonate, poly(diallyldimethylammonium chloride), polyethylene terephtalate, or polyamide (nylon). The adhesion module may further comprise a supportive porous layer on the basal side of the semi-permeable membrane. The material of the supportive porous layer is poly(diallyldimethylammonium chloride), poly(acrylic acid) or combinations thereof.

In another embodiment of the invention the basal compartment of the module comprises viable cells. The cells can be Caco-2 cells and/or HT29 cells. The cells can grow in a monolayer with their apical side towards the semi-permeable membrane. The apical side of the cells can optionally be covered with a protective mesh.

In a further embodiment of the invention the module comprises beads, having from inside out, an inner support layer, a semi-permeable membrane and an artificial mucus layer. Said beads have a radius between 500 µm and 1 cm, in particular between 500 µm and 5 mm. The inner support layer can comprise biochemical slow release oxygen components. Alternatively, the inner support layer can be covered with an intermediate layer containing biochemical slow release oxygen components.

The surface area of the artificial mucus layer is about and between 1 cm$^2$ and 200 m$^2$, in particular about and between 1 cm$^2$ and 1000 cm$^2$, in particular about and between 1 cm$^2$ and 100 cm$^2$. One or more microorganisms can be attached to the mucus layer and optionally form colonies or a biofilm.

Another aspect of the invention relates to an in vitro system comprising the above described adhesion module. The in vitro system can be an in vitro gastrointestinal model, an in vitro female reproductive tract model, an in vitro mouth soft epithelium model or an in vitro respiratory tract model. This in vitro system can be an in vitro gastrointestinal model comprising one or a combination of a stomach compartment, a small intestine compartment, an ascending colon compartment, a transverse colon compartment, and a descending colon compartment. The small intestine compartment can be replaced by a duodenum compartment, a jejunum compartment and an ileum compartment. The adhesion module of the invention can be put in parallel and/or in series with one of the compartments.

Yet, a further embodiment of the invention relates to a method of determining the effect of an element on the above described adhesion module, said method comprising: (a) introducing said element into said module or said system; and (b) determining whether any change occurs in any characteristic or feature/function of interest of said module or said system in the presence of said element or subsequent to the introduction of said element into said module or said system, wherein said change is indicative that said element has an effect on the module or the system. Thus this embodiment of the invention also relates to the use of the adhesion module or the in vitro system as described above for the study of the effect of an element. This embodiment of the invention also relates to the use of the adhesion module or the in vitro system as described above for the study and modulation of the molecular signalling and adaption between the host cells and the microorganism optionally after the addition of an element and for the study and modulation of physiology, metabolic activity or probiotic or pathogenic characteristics of their flora optionally after the addition of an element.

The element is selected from the group of
(a) a microorganism;
(b) a substrate;
(c) a chemical substance;
(d) a cell; and
(e) any combination of (a) to (d).

Yet, another aspect of the invention relates to the use of the adhesion module or the in vitro system as described above for the study and the treatment of a disorder related with an impaired mucosal barrier, in particular with an impaired mucosal adhesion. The disorder can be associated with the invasion by antigens that cause allergic reactions, can be associated with the mucosal adhesion and invasion by pathogens, a metabolic disorder or a chronic colonic disease.

BRIEF DESCRIPTION OF THE FIGURES

FIG. 2. Scheme of the adhesion modules comprising two chambers where

DETAILED DESCRIPTION

Figure 1:
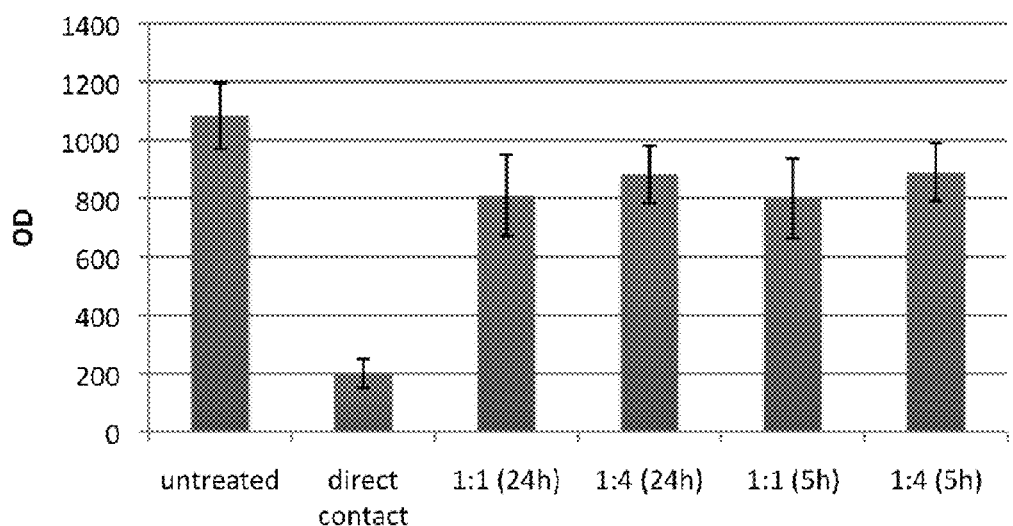
FIG. 1. MTT test conducted on Caco-2 cells to evaluate the cells viability under different conditions.

The adhesion module of the present invention comprises 2 compartments separated by a semi-permeable membrane; said membrane having an artificial mucus layer applied on its luminal side; and said module being characterized by having anaerobic conditions at its luminal side and aerobic conditions at its basal side.

With the term "module" or "adhesion module" is meant an excipient (e.g. a vessel or a container) wherein the environmental conditions of a mucosal layer are mimicked.

The combination of the mucus layer and the semi-permeable membrane, for dividing the adhesion module in 2 compartments, is hereinafter also referred to as the functional layer. Said functional layer can be a double, triple or multi-layer, but consists of at least two layers wherein the first layer, i.e. the top layer or the layer in direct contact with the luminal compartment, is the artificial mucus layer and the second layer is the semi-permeable membrane. With the term "luminal compartment" is meant the compartment simulating the lumen of the tract of the host. With the term "basal compartment" is meant the compartment at the opposite end of the functional layer when compared to the luminal compartment. With the term "luminal side of the mucus layer" is meant the side of the mucus layer in contact with the simulated lumen of the host. With the term "basal side of the mucus layer" or "basal side of the functional layer" is meant the side opposite to the luminal side.

The functional layer can serve different objectives including but not limited to transport of fluid, substances and/or gases and support for microorganisms.

When the functional layer consists of a double-layer, one layer is the mucus layer and the other layer is a semi-permeable membrane.

The mucus layer is always on the luminal side of the adhesion module. The semi-permeable membrane is always on the basal side of the mucus layer. When the functional layer is a triple or multi-layer, it can comprise a mucus layer, a semi-permeable membrane and a supportive layer, either the semi-permeable membrane or the supportive porous layer can be next to the mucus layer, preferably the semi-permeable layer is next to the mucus layer.

Hence, the functional layer comprises a semi-permeable membrane, which allows transport of oxygen from the basal to the luminal compartment and the transport of low molecular weight microbial metabolites or digested food components from the luminal to the basal compartment of the module and vice versa. The delivery of oxygen from the basal to the luminal side is crucial for establishing microaerophilic conditions prevailing at the interface between the biofilm and the mucus layer.

With "microaerophilic condition" is meant the condition obtained when the aerobic condition in the basal compartment of the module results in a partial oxygen pressure, at the basal side of the mucus layer of about and between 1-150 mm Hg and preferably of about and between 1-45 mm Hg, which is in correspondence with values characteristic for the in vivo situation.

Life common to the majority of animal and plants species requires the presence of oxygen. With "aerobic condition" is meant the condition required for growth or metabolism in which said organisms are sufficiently supplied with oxygen. For example, various genera of bacteria have differing needs for oxygen. Some, like *Clostridium*, find oxygen toxic and usually do not grow in air. Others can grow only when oxygen is present. Depending on the oxygen relationship, bacteria can be classified in the following groups based on their growth in Glucose Shake Tubes (GST);

AA=strict anaerobes: *Clostridium, Sarcina*, and many genera from the rumen of cattle, intestines and similar sites. Strict anaerobes grow only were oxygen is absent. Some are more sensitive to oxygen than others. Some species, especially those from the rumen and intestines, die rapidly when exposed to oxygen. Most *Clostridium* species are not killed by such brief exposure but cannot grow in oxygen. Some species of *Clostridium* can grow slowly in the presence of air. No species of *Clostridium* is able to produce spores when free (uncombined) oxygen is present;

FA=facultative anaerobes: *Escherichia, Citrobacter, Enterobacter*, and *Proteus* grow best in oxygen but can grow in the absence of oxygen by stealing oxygen from foods such as nitrate, sugars, and other "honorary oxygens". The result of this is production of nitrite, organic acids (lactic acid, formic acid, etc.), and other substances which are often foul-smelling. Tubes containing facultative anaerobes contain growth throughout when the bacteria are evenly distributed, but there is usually a heavier growth on the surface of the agar because they grow best in air;

MA=microaerophilic: *Azospirillum, Aquaspirillum, Cytophaga* require oxygen but grow best just below the surface of the agar where oxygen is reduced. This type of bacteria is relatively uncommon in laboratories because some will not grow on GST and other common media. It is difficult to find a species which will grow in a well defined band a millimeter or so below the surface to produce a mice band below the surfarce as seen here. Often the band is so near the surface that you can confuse these for aerobic species, however, they do not grow profusely on the surface of the agar like aerobic species;

A=strict aerobes: *Acetobacter, Arthobacter, Azomonas, Bacillus, Micrococcus, Pseudomonas, Xanthomonas* grow only on the surface of the agar where they get plenty of oxygen. Most produce a heavy growth above the agar which may be a liquid. Some bacteria produce slimes or capsules and these produce exceptional profuse growth above the agar and may burrow into the agar slightly. The liquid containing cells may run down between the walls of the tube and the agar plug, but you should not confuse this with growth; and I=indifferent: *Lactobaccilus*, some *Streptococcus*, and most other milk organisms grow equally well on the surface and within the agar because they are indifferent to the oxygen level. Notice that the bacteria grow uniformly on the surface and to the bottom of tube provided the cells are distributed uniformly. The growth is similar to that of facultative anaerobes except FAs have a heavy growth of bacteria at the surface. At the surface indifferent bacteria may have barely noticeable growth of cells. We know they can grow on the surface because they do so when spread on a petri plate. Actually, many of these bacteria require vitamines, amino acids, and other growth factors and the colonies may be tiny even on the media most suitable for them.

As such "anaerobic condition" is meant the condition required for growth or metabolism of an organism which does not require oxygen, such as the AA bacteria above. In a particular embodiment of the present invention "anaerobic conditions" correspond to an oxygen concentration below 0.5 mg/L.

With the term "semi-permeable membrane" is meant a membrane that allows the transport of components ranging between 0 and 100000 Da, in particular between 1-10000 Da, more in particular between 0 and 5000 Da, even more in particular between 0 and 1000 Da. An example of the membrane material for the semi-permeable membrane includes but is not limited to polycarbonate (PC), poly(diallyldimethylammonium chloride) (PDDA), polyamide (PA) or polyethylene terephtalate. The function of the semi-permeable membrane is to differentiate between compounds that can or cannot be transported across the membrane. When the functional layer consists of a mucus layer and a semi-permeable layer only, then the semi-permeable layer can also support the mucus layer and optionally a biofilm.

Examples of the material for the supportive layer include but are not limited to poly(diallyldimethylammonium chloride) (PDDA), poly(acrylic acid) (PAA), or combinations thereof. With the term "supportive porous layer" is meant a layer that allows the transport of any type of compound as its function is only support of, for example, the above semi-permeable membrane and the mucus layer and optionally a biofilm.

The term "mucin" is used herein to mean a protein obtained as the result of the expression of a mucin gene. Human mucin genes include but are not limited to muc1, muc2, muc3, muc4, muc5, much, muc7, muc8 and muc9 and their relative subclasses such as but not limited to muc5B and muc5AC. Within the meaning of this term, mucin encompasses all proteins encoded by a muc gene, mutants thereof, alternative splice proteins thereof, and glycosylated proteins thereof. Additionally, as used herein, the term "mucin" includes mucin analogues and mucin homologues and analogues of other animals. Examples of mucin homologues and analogues include but are not limited to the two discrete types of mucin proteins that exist in the mouse intestine; secretory Muc2 and membrane-bound Muc3, as well as mouse Muc1 in the gallbladder, or Muc2 in the chicken The artificial mucus layer is determined by 2 parameters: the type of mucin and the thickness of the mucus layer. Both parameters can depend on the site and the state of being of the organism to be simulated. The mucus layer allows the adhesion of microbial cells, formation of aggregates and colonies and further colonization to a biofilm.

Examples of mucin types include but are not limited to
  gel-forming Muc2 and non-gel forming Muc1 proteins when the intestine is simulated,
  six different Muc gene products in the cervix when different phases of the menstrual cycle in the cervix are simulated,
    secreted Muc5B and Muc7 and membrane-associated mucins, Muc1, Muc4, and Muc16 in the oral cavity,
  Muc1 protein backbones with different carbohydrate side-chains depending on simulation of the respiratory or the intestinal tracts.

Figure 2A:
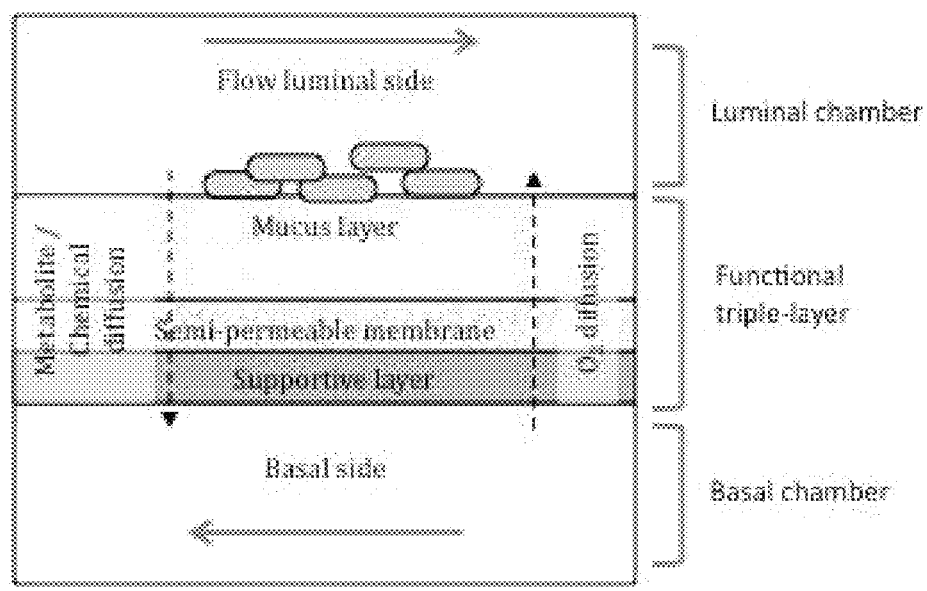
FIG. 2A is an adhesion module with a functional layer comprising a mucus layer, a semi-permeable membrane and a supportive layer; where the flow into the luminal chamber is in a counter current direction from the flow into the basal chamber.
Figure 2B:
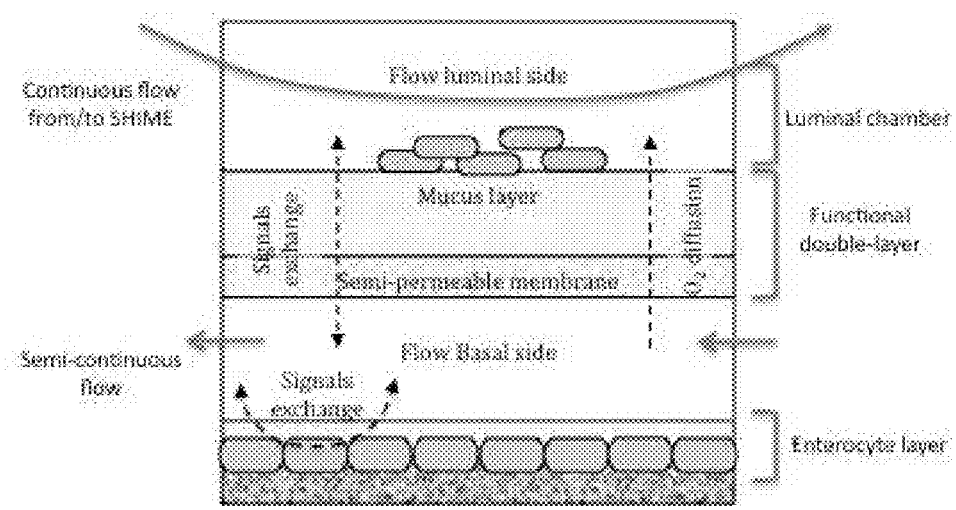
FIG. 2B is an adhesion module with a functional layer comprising a mucus layer and a semi-permeable membrane wherein in the basal chamber cells are grow in a monolayer with their apical side towards the mucus layer.

The thickness of the mucus layer can be varied between 1 μm and 1000 μm (FIG. 2). This mucus layer can be loosely adherent or firmly adherent depending on the mucin type (gel forming or non-gel forming mucins) and water concentration. Preferably the thickness of the mucus layer (FIG. 2);
  is between 178-200 μm, even more preferable between 75-85 μm for the firmly adherent mucus layer and between 97-121 μm for the loosely adherent mucus layer, when simulating the corpus,
  is between 233-315 μm, even more preferable between 138-170 μm for the firmly adherent mucus layer and between 82-158 μm for the loosely adherent mucus layer, when simulating the antrum,
  is between 132-208 μm, even more preferable between 13-19 μm for the firmly adherent mucus layer and between 115-193 μm for the loosely adherent mucus layer, when simulating the duodenum,
  is between 119-127 μm, even more preferable between 13-17 μm for the firmly adherent mucus layer and between 103-113 μm for the loosely adherent mucus layer, when simulating the jejunum,
  is between 433-527 μm, even more preferable between 24-34 μm for the firmly adherent mucus layer and between 400-494 μm for the loosely adherent mucus layer, when simulating the ileum,
  is between 720-940 μm, even more preferable between 65-167 μm for the firmly adherent mucus layer and between 605-823 μm for the loosely adherent mucus layer, when simulating the colon,
  is between 5 and 150 μm in the respiratory system,
  is between 150 and 470 μm in the oral cavity, and
  is between 100 and 250 μm in the vaginal tissue The extent of colonization is affected by shear forces of the intestinal suspension along the mucus layer. With the term "shear force" is meant: a stress which is applied parallel or tangential to a face of a material, as opposed to a normal stress which is applied perpendicularly. Shear forces are influenced by the peristaltic movements and the hydrolic residence time. For example, the high peristaltic movement in the upper intestine (duodenum, jejunum) creates high shear forces of 15 to 40 dynes/cm$^2$ as well as a residence time (1-4 h), which are too short for microorganisms to efficiently colonize the respective mucosa. In contrast, the peristaltic movement at the terminal ileum is much lower as well as the shear forces (below 10 dynes/cm$^2$), thus creating a residence time (5-8 h) that allows bacteria to efficiently colonize the tract. Finally, in the colon the shear forces decrease to values of 2.5 dynes/cm$^2$.

Preferably, the shear forces and residence times:
are 15-20 dyne/cm$^2$ with a residence time of 1 hour when simulating the upper part of the small intestine,
are 8-12 dyne/cm$^2$ with a residence time of 2 hour when simulating the lower part of the small intestine,
are 4-6 dyne/cm$^2$ with a residence time of 10 hour when simulating the upper part of the colon,
are 2-3 dyne/cm$^2$ with a residence time of 24 hour when simulating the lower part of the colon,
are 0.5-3 dyne/cm$^2$ when simulating the respiratory tract at rest breathing (it can reach 1700 dyne/cm$^2$ with cough and bronchospasm).

By using a flow cell setup, the flow rate and flow velocity and hence the shear force over the mucus layer can be modified.

As the surface area of this mucus layer can be quite limited (ca. 100 cm$^2$) when present in a functional layer, the intestinal suspension is recycled several times to increase the residence time to relevant values for the gut compartment of interest and to increase the efficiency in the module absorption. The number of cycles can vary between 1 and 100.

In another embodiment of the invention the basal compartment of the module can comprise viable cells.

With the term "cell" is meant any primary cell or cell line derived from all kind of tissues. The embodiment with cells in the basal compartment, allows the indirect and continuous interaction between the growing biofilm and the cells, with exchange of signal molecules.

Examples of a cell include but are not limited to enterocytes, endothelial cells, dendritic cells, monocytes, macrophages, vaginal or oral epithelial cells (keratinocytes) and/or lymphocytes.

Preferably, the primary cell or cell line is an enterocyte. The cells in the basal compartment simulate the host such as, for example, the epithelium of the gastrointestinal tract of the host, hence the basal compartment can include an artificial environment to study the host-microbiota interactions. An example of cell lines for host simulation include but is not limited to Caco-2 or HT29 cell lines.

The different cells can be mixed and combined in different proportions. Preferably, the proportion Caco-2 cells versus HT 29 cells is 1 to 3 (Nollevaux et al., 2006). The cells can grow to form a monolayer or aggregates, in a suspension or on beads. When the cells are grown in monolayers, they can grow on the bottom of the basal chamber or on a semipermeable membrane or a supportive layer. When the cells grow on a surface or a bead, these surfaces or beads can be coated with collagen type I in order to improve adherence (Straubb et al., 2007). When the cells are present on a semi-permeable membrane and/or a supportive porous layer, they can form a separated second layer, that can be a functional layer. The cells can also be part of the functional layer dividing the adhesion module in a luminal and a basal compartment. The cells can grow with there apical side towards the functional layer or away from the functional layer. Preferably, the cells grow with their apical side towards the functional layer. The apical side of the cells can be covered with a protective mesh to protect the cells against for example flow and/or shear force.

To avoid cytotoxicity phenomena and/or in order to be able to detect certain elements including but not limited to signal molecules, a continuous or semi-continuous flow of fresh medium can be applied to the basal compartment within an appropriate timeframe. With the term "semi-continuous" is meant that at well-defined time points and within well defined time periods, quantities of the cell medium are removed and replaced by fresh medium. Total volume of the medium to be replaced can be between 0.5 and 50 mL.

The surface area of the mucus layer in the adhesion module with a luminal and a basal chamber can be between 1 and 1000 cm$^2$ in particular between 1 cm$^2$ and 100 cm$^2$.

Figure 3:
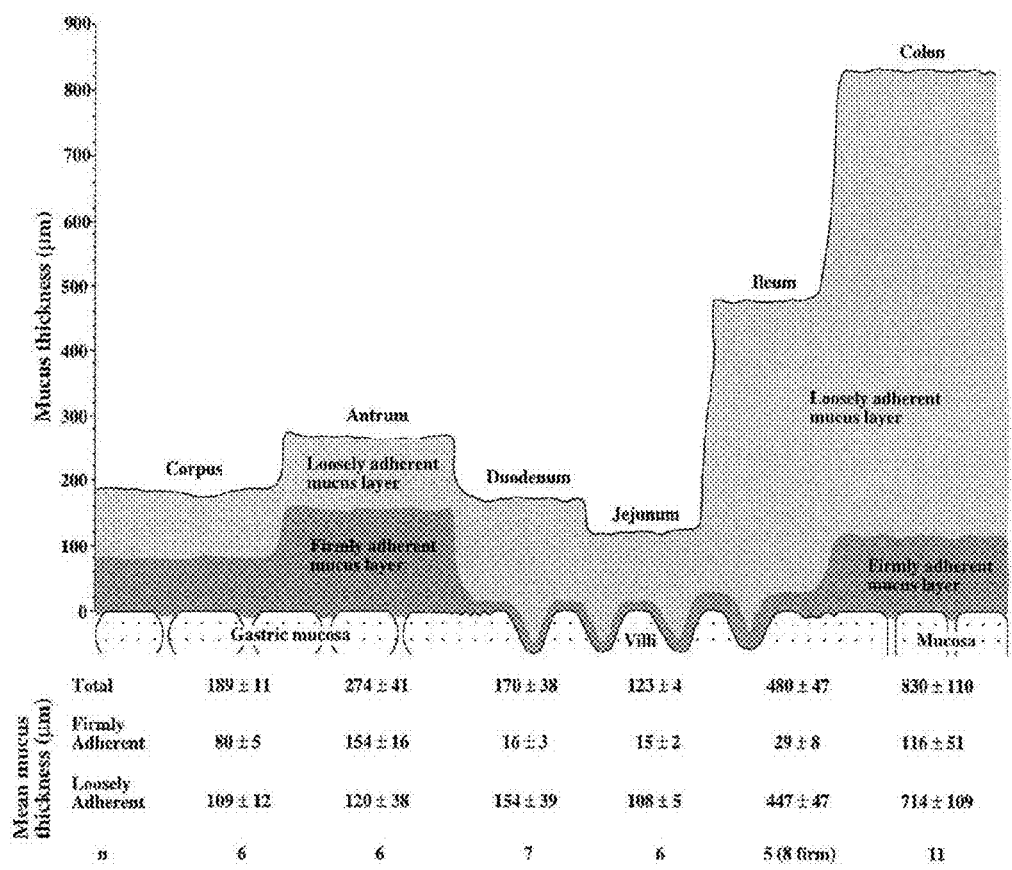
FIG. 3: Mucus thickness along the different zones of the GI tract (Atuma et al., 2001).
Figure 4:
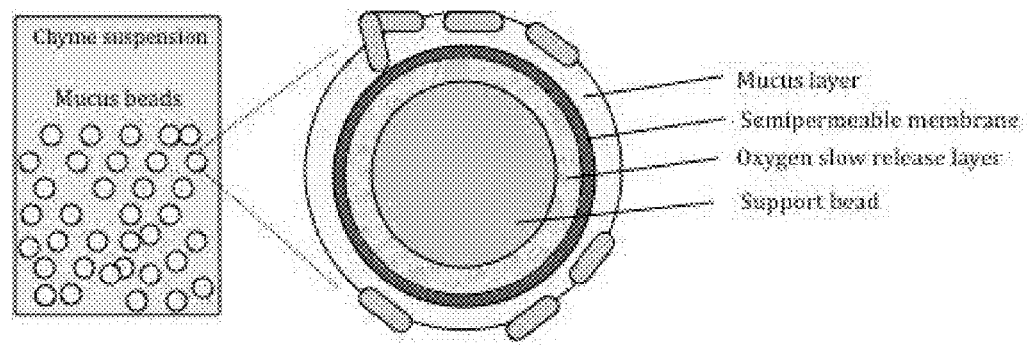
FIG. 4: Scheme of mucus coated beads comprising an inner support bead, an intermediate layer comprising slow oxygen release material, a semi permeable membrane and a mucus layer.
Figure 5:
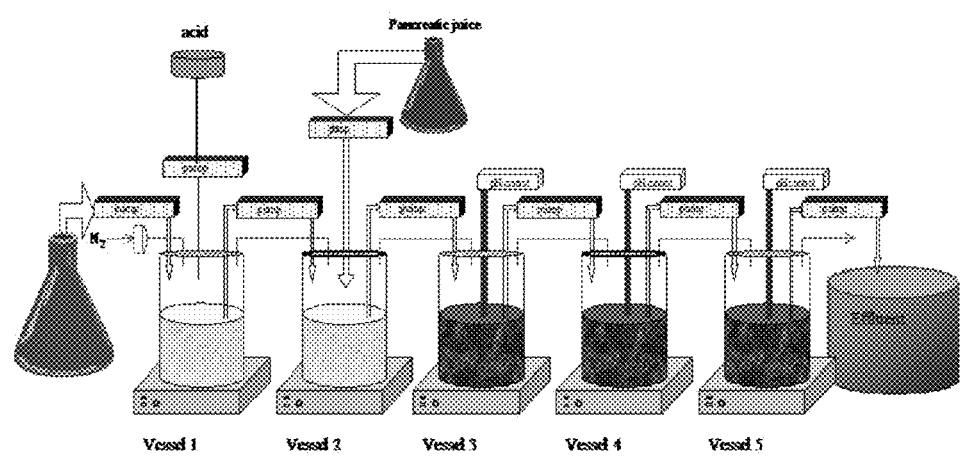
FIG. 5: Schematic representation of the conventional SHIME

In another embodiment of the invention the adhesion module comprises beads, having from inside out, an inner support bead, a semi-permeable membrane and an artificial mucus layer (FIG. 3). US25186633 describes a biofilm reactor in which gel beads are used in a biofilm reactor.

In order to have relevant oxygen concentrations at the base of the biofilm the beads used in the present embodiment of the invention are characterized by a slow oxygen release material. In these beads oxygen is released in an amount as described above. In one embodiment of the invention, the beads are assembled of an inner support bead comprising biochemical slow release oxygen components. The inner support bead can also be covered with an intermediate layer containing biochemical slow release oxygen components. Oxygen is released in an amount as described above.

The inner support bead comprising the biochemical slow release oxygen components or the intermediate layer containing the biochemical slow release oxygen components, is covered with a semi-permeable membrane and an outer mucus layer comprising the mucins as described above. The inner support bead comprising the biochemical slow release oxygen components or the oxygen-releasing intermediate layer, can be further separated from the semi-permeable membrane and the outer mucus layer by a supportive layer permeable to oxygen.

In an alternative embodiment of the aforementioned beads, the inner support bead is not present and the slow oxygen release material is within a porous bead instead.

When the adhesion module of the invention comprises beads, with the term "the luminal side of said module" is meant the inner environment of the adhesion module that is in direct contact with the outer surface of the bead and with the term "the basal side of said mucus layer" is meant the side of the mucus layer faced inwardly to the center of the beads.

The radius of the beads used in the biofilm reactor is between 500 µm and 1 cm, more in particular between 500 and 5 mm. As an example, 1000 beads of a radius of 5 mm would result in a specific surface area of around 3140 cm$^2$, which is more relevant to approach large surface area values as described in the in vivo situation.

In the above described adhesion module the surface area of the mucus layer can be between 1 cm$^2$ and 200 m$^2$. One or more microorganisms can attach to the mucus layer and optionally form colonies or a biofilm.

The terms "in vitro model of the invention" and "in vitro system of the invention" are interchangeable and are used herein to indicate a model and or system comprising an adhesion module as described above.

The adhesion module of the present invention can be included in an in vitro gastrointestinal model, an in vitro female reproductive tract model, an in vitro respiratory tract model, an in vitro oral mucosa model or any other model comprising a soft epithelium covered by a mucus layer The adhesion module of the present invention can be included, put in parallel or put in series with the different compartments in different in vitro models. One, two or more adhesion modules can be implemented in the different in vitro models. Preferably, an adhesion module is put in parallel with one of the compartments of an in vitro system.

Examples of the different compartments that allow implementation of the adhesion module of the present invention include but are not limited to models simulating the compartments of the female reproductive tract, of the mouth soft epithelium, or of the respiratory tract.

Furthermore, the adhesion module of the present invention can be placed in parallel with or between the different compartments of the SHIME—the Simulator of the Human Intestinal Microbial Ecosystem. The continuous adhesion module can be implemented in, next to or after:
the stomach compartment,
the small intestine compartment,
the ascending colon compartment,
the transverse colon compartment, or
the descending colon compartment.

The SHIME can be further developed to better simulate the in vivo situation. In the in vivo situation, the terminal ileum is considered the place where significant colonization by microorganisms (>7 log CFU/g) takes place. An extension of the SHIME can thus be made where the duodenum, jejunum and ileum are separately mimicked. A gradual pH correction with $NaHCO_3$, a more precise secretion of pancreatic enzymes and bile salts and a control of the retention times characterize the digestive processes and conditions in the duodenum. This enzymatic small intestine digestion is further maintained in the jejunum compartment. The extension of the SHIME model lies in the incorporation of a microbiological component in the ileum compartment. A microbial community is grown here through initial reflux colonization from the ascending colon. The shorter residence times, higher bile salt and enzyme concentrations in the ileum compartment will lead to an adapted microbial community which represents both in composition as in metabolic activity that of the in vivo terminal ileum.

Thus, the adhesion module of the present invention can also be implemented in the different compartments of the extended SHIME. The continuous adhesion module can be implemented in, next to or after:
the duodenum compartment,
the jejunum compartment, or
the ileum compartment.

In another aspect, the invention further provides for an in vitro system comprising the adhesion module of the invention.

In another aspect, the invention further provides a method of determining the effect of an element on the adhesion module or the in vitro system, said method comprising: (a) introducing said element into said module or said system; and (b) determining whether any change occurs in any characteristic or feature/function of interest of said module or said system in the presence of said element or subsequent to the introduction of said element into said module or said system, wherein said change is indicative that said element has an effect on the module or the system.

The term "change in any characteristic or feature/function of interest of said module" includes, but is not limited to a modulation of;
a) the growth and/or activity of one or a limited number of non pathogenic or beneficial microorganisms. Examples of non-pathogenic or beneficial microorganisms include but are not limited to lactobacilli, bifidobacteria, butyrate- and/or propionate-producing bacteria,
b) the growth and/or activity of one or a number of pathogenic microorganisms. Examples of pathogenic microorganisms include but are not limited to *Bacillus cereus, Candida albicans, Clostridium perfringens* and/or *C. difficile,*
c) the growth and/or activity of one or a number of cells and cell lines derived therefrom. Examples of cell types include but are not limited to enterocytes, epithelial cells, endothelial cells, dendritic cells, monocytes, macrophages, T-cells and/or B-cells.
d) the attachment of beneficial, non-pathogenic, or pathogenic microorganisms to the mucosa of the above mentioned systems,
e) the uptake or release of signalling molecules including but not limited to antigens, pro- and anti-inflammatory molecules, receptors, products of both microorganisms and/or the cells simulating the host. Examples of said signalling molecules include but are not limited to antibodies, hormones, cytokines, bacterial lipopolysaccharide, proglucagon, GLP-1, GLP-2 and/or FIAF,
f) up- and down-regulation of genes at DNA, RNA or protein level by both microorganisms and/or the cells simulating the host,
g) the production of specific bacterial metabolites such as but not limited to propionate and/or butyrate, and/or
h) the reciprocal adaptation of the cell types simulating the host and/or the microorganisms.

The term "modulation" includes but is not limited to an increase, a stimulation, a decrease, an inhibition or a reduction.

The term "molecular signalling" includes but is not limited to any characteristic, feature/function described under (e), (f) and (g) above.

The term "adaptation" includes but is not limited to any change in any characteristic or feature/function of interest described under (a) to (g) that occurs in a cell, cell line and/or microorganism in response to a change in any characteristic or feature/function of interest described under (a) to (g) that occurs in any other cell, cell line and/or microorganism.

The term "host cellular response" includes but is not limited to any change in any characteristic or feature/function of interest described under (a) to (g) that occurs in a cell in the basal chamber of the module.

An element as described above or below is selected from the group consisting of:
(a) a microorganism;
(b) a substrate;
(c) a chemical substance;
(d) a cell; and
(e) any combination of (a) to (d).

An example of a microorganism includes but is not limited to a virus, a bacterium (probiotic, commensal or pathogen), a yeast or a mold. An example of a substrate includes but is not limited to a foodstuff, a prebiotic, a synbiotic or a dietary fiber. An example of a chemical substance includes but is not limited to a small molecule (e.g. an antibiotic), a peptide, a hormone, a cytokine, a pro- and anti-inflammatory product, a bacterial product or metabolite or a viral constituents. An example of a cell includes but it is not limited to an enterocyte, an epithelial cell, an endothelial cell, a dendritic cell, a monocyte, a macrophage and/or a lymphocyte.

Another aspect of the invention provides for the use of the module of the invention or the system of the invention for the study and modulation of the molecular signalling and adaptation between the simulated host and the microorganism optionally after the addition of an element.

Another aspect of the invention provides for the use of the module of the invention or the system of the invention for the study of the effect of an element on the flora, in particular on the adhesion of the flora.

Another aspect of the invention provides for the use of the module of the invention or the system of the invention for the study of the composition, activity and adhesion of the flora under different environmental conditions.

Another aspect of the invention provides for the use of the module of the invention or the system of the invention for the control and modulation of physiology, metabolic activity or probiotic or pathogenic characteristics of the flora.

Another aspect of the invention provides for a method comprising culturing microorganisms in the above-noted module or system and controlling or adjusting culture conditions with regard to the element or functional aspect and effect thereof on the flora, in particular on the adhesion of the flora Another aspect of the invention provides for a method comprising culturing microorganisms and cells in the above-noted module or system and allowing adaptation to study the reciprocal effect, in particular the adhesion of the flora, and/or the cellular response detectable by production of a peptide, a hormone, a cytokine and/or a pro- or anti-inflammatory product.

Thus the adhesion module of the invention when implemented in for example the SHIME or the extended SHIME can be used to study the effects of different factors on both composition, metabolic activities and adhesion of the gastrointestinal flora and the host cells. It can be used to study the mixed bacterial populations of the large intestine. It can provide a reproducible baseline for studying the ecology of the gut ecosystem, particularly the changes induced in adhesion after perturbation of the flora by diet, drugs and a large variety of products and chemicals and the respective effects in terms of host cellular response. This adhesion module of the invention when implemented in the SHIME or the extended SHIME can be used for developing and testing probiotic, prebiotic or synbiotic foods and their effects on the gastrointestinal microflora in particular their effects on adhesion and the respective host cellular response. It may also be used to test intestinal flora sampled from an ill animal (e.g. a mammal [e.g. a human]) or unbalanced flora.

Thus the adhesion module of the invention when implemented in the SHIME or the extended SHIME can be used to maintain a microbial population which can serve as an inoculum for short time batch culture experiments to test, for example, adhesion characteristics, growth kinetics or toxin production of microbial samples and to test the host cellular response in challenging in vitro cells with mixed microbial communities.

Another aspect of the invention provides for the use of the module of the invention or the system of the invention for the study of the effect of an element on the module or the system, in particular to assess the effect of different treatments that could be used to modulate the adhesion of their flora, or of the host cellular response, and eventually treat the patient.

Another aspect of the invention provides for the use of the module of the invention or the system of the invention for the study and the treatment of disorders related with an impaired mucosal barrier, in particular with an impaired mucosal adhesion.

Another aspect of the invention provides for a method comprising culturing microorganisms in the above-noted module or system and controlling or adjusting culture conditions with regard to the element or functional aspect and effect thereof on the module or the system, in particular with regard to adhesion of their flora and the host cellular response and the effect thereof on the module or the system.

Another aspect of the invention provides for a method comprising culturing microorganisms in the above-noted module or system to assess the effect of different treatments that could be used to modulate an impaired mucosal barrier, in particular with an impaired mucosal adhesion and eventually treat the patient.

The term "treating" or "treatment" as used herein covers any treatment of a disease and/or condition in an animal, particularly a human, and includes: (i) preventing a disease and/or condition from occurring in a subject which may be predisposed to the disease and/or condition but has not yet been diagnosed as having it; (ii) inhibiting the disease and/or condition, i.e., arresting its development; (iii) relieving the disease and/or condition, i.e., causing regression of the disease and/or condition.

Invasion by antigens that cause allergic reactions is associated with an impaired mucosal barrier. Such allergens may comprise certain food substances, chemicals and other molecules. Thus in a further embodiment, the present invention provides for the use of the adhesion module or the system of the invention in the study and the treatment of conditions associated with the invasion by antigens that cause allergic reactions (e.g. food allergies, asthma, eczema).

The adhesion module or system of the invention can be used to evaluate mucosal attachment and invasion by pathogens, such as certain species of *Clostridium, Escherichia, Salmonella, Shigella* and *Pseudomonas*, as well as yeasts such as *Candida albicans* and the consequent host cellular response. Thus in a further embodiment, the present invention provides the use of the adhesion module or system of the present invention in the study and treatment of conditions associated with the mucosal adhesion and invasion by pathogens (e.g. air-way, vaginal, eye, ear infections, acquired diarrhea and traveler's diarrhea).

The intestinal microbiota impacts energy and metabolic homeostasis of the host, i.e. control of food and energy intake, food and energy metabolism, fat mass development, and associated metabolic disorders such as obesity and type 2 diabetes (Cani and Delzenne, 2007). Hence, a further embodiment of the present invention, provides for the use of the adhesion model or the system of the invention for the study and the treatment of metabolic disorders.

Also inflammatory bowel disease (IBD) is associated with an impaired gastrointestinal mucosal barrier. It is generally accepted that in IBD, gastrointestinal mucosal injury with an impaired resolution of the lesions is one of the key elements that lead to these chronic indication. IBD also referred to as "chronic colonic diseases", as used herein include any condition characterized by persistent mucosal injury at different levels of the gastrointestinal tract, and consequent host overreaction, such as for example inflammatory bowel syndrome, mucositis, gastric ulcers, Crohn's disease, ulcerative colitis, colorectal cancer and pouchitis. It is accordingly a further embodiment of the present invention, to provide the use of the adhesion model of the system of the invention for the study and the treatment of chronic colonic diseases.

Another aspect of the invention provides a system comprising 3 compartments: a luminal side with the microbial community, a basal compartment with the host cell lines and, below the latter, a third compartment simulating the blood stream. This module can be used to investigate the rate of absorption of e.g. active compounds, following the microbial metabolism and the diffusion through the mucus layer and the simulated gut surface.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. In the claims and the description, the word "comprising" and every example given is used as an open-ended term, substantially equivalent to the phrase "including, but not limited to".

The following examples are illustrative of various aspects of the invention, and do not limit the broad aspects of the invention as disclosed herein.

EXPERIMENTAL PART

1. Set-Up of the GIT Model

The most basic adhesion module according to the present invention, consists of a luminal chamber (upper compartment) containing growth medium and the inoculated bacterial strain(s) and a basal chamber (lower compartment) in which oxygen pressure can be regulated and from which oxygen is allowed to diffuse across a separating layer into the luminal chamber. The separating layer is a semi-permeable membrane, allowing diffusion of oxygen and signal molecules and which on its luminal side is covered with an artificial mucus layer, relevant for the specific region of the gastrointestinal tract. Said mucus layer being a mucin-agar layer of a certain thickness, poured on top of the membrane using an Automatic Biofilm Applicator (Elcometer 4340).

2. Mucus Resistance to a Shear Stress

In a first test of the GIT model according to the invention, the capacity of the mucus layer to firmly adhere to the membrane and to resist to the mechanical removal by a shear stress was evaluated. Three types of membrane material were tested: hydrophilic polycarbonate, polyamide and polycaprolacton. The latter was immediately discarded because it was very complex to handle during the subsequent procedures. A mucin-agar layer of 200 μm was poured on the top of the membrane using an Automatic Biofilm Applicator (Elcometer 4340). FITC-dextran (4 KDa) was added to the mucus layer for further analysis of the mucus integrity by means of Laser Scanning Confocal Microscopy (LSCM). The so-formed double-functional layer was then incorporated in the adhesion module and two different shear stresses (i.e. 10 and 20 dynes/cm$^2$) were applied for a time of 5 hours (T5). Analysis by LSCM of the mucus layer on a vertical section and comparison of T0 with T5 led to the following conclusions: 95% of the original mucus layer was still present after 5 hours at medium shear stress (10 dynes/cm$^2$) and 45% at high shear stress (20 dynes/cm$^2$) for both hydrophilic polycarbonate and polyamide.

3. Compounds Permeation Through the Double Functional Layer

The second test was conducted to evaluate the permeation through the double functional layer (membrane and artificial mucus layer) of different compounds, simulating possible metabolites (of prokaryotic or eukaryotic origin) of different dimensions and molecular radius. FITC-conjugated dextran of 4 kDa, 20 kDa, and 150 kDa were used as model compounds. A standard curve based on the molar concentration was created for each compound. Permeability was assessed using a double functional layer both with a polyamide (pore size: 0.5 mm) and a polycarbonate (pore size: 0.4 mm) membrane. Table 2 provides the results for the different compounds in the adhesion module with both types of membrane with and without a 200 μm mucus layer.

The permeability coefficient was calculated according to the following formula $$P_c = \frac{(C_{u4} - C_{u0.5})V^*}{AtC_0}$$

where $C_{u0.5}$ and $C_{u4}$ are the concentrations of FITC-conjugated dextran in the lower chamber at 0.5 and 4 hours, respectively, $V^*$ is the chamber volume, A is the surface area of the exposed membrane, $C_0$ the initial concentration in the upper chamber, and t is the duration of the steady state flux (3.5 hours).

TABLE 2

Compounds permeation through the double-functional layer. Data (permeability coefficient) are expressed as cm/sec.

| FITC-dextran | Polyamide membrane | | Polycarbonate membrane | |
|---|---|---|---|---|
| | No mucus | Mucus | No mucus | Mucus |
| 4 kDa | $1.5 \cdot 10^{-5}$ | $3.55 \cdot 10^{-6}$ | $6.64 \cdot 10^{-5}$ | $3.96 \cdot 10^{-5}$ |
| 20 kDa | NT | NT | $3.08 \cdot 10^{-5}$ | $2.55 \cdot 10^{-5}$ |
| 150 kDa | $4.05 \cdot 10^{-6}$ | $4.46 \cdot 10^{-8}$ | $2.53 \cdot 10^{-5}$ | $4.91 \cdot 10^{-6}$ |

NT = not tested

4. Establishment of Microaerophilic Conditions in the Double Functional Layer

The adhesion module was built with a functional double layer separating the completely anaerobic upper chamber (95% $N_2$-5% $CO_2$) from the aerobic lower chamber (95% $O_2$-5% $CO_2$). Oxygen concentration in the upper chamber was measured by means of a Hach Lange luminescent LDO oxygen probe. Experiments were conducted at room temperature with a 200 μm-thick mucus layer using a polycarbonate or a polyamide membrane. Data of the increasing oxygen concentration in the upper chamber, collected in the first 30 minutes, were used to calculate the relative permeability ($Pm_{O2}$). $Pm_{O2}$ for the polycarbonate membrane resulted to be $4.9 \cdot 10^{-4}$ cm/sec with a relative diffusion coefficient ($D_{O2}$) of $9.8 \cdot 10^{-6}$ cm$^2$/sec; and for polyamide, $Pm_{O2}=2.5 \cdot 10^{-4}$ cm/sec, $D_{O2}=5.0 \cdot 10^{-6}$ cm$^2$/sec.

5. Adhesion Potential of Pure Bacterial Cultures Vs Mixed Microbial Communities

A first objective of working with the in vitro adhesion module is to explore the adhesion potential of pure cultures of gut microorganisms vs mixed microbial communities onto a mucus-covered layer. A culture of *Lactobacillus rhamnosus* GG was grown in relevant medium and inoculated in the luminal chamber of the adhesion module. The luminal chamber of a second system was inoculated with an in vitro adapted microbial community originated from the ascending colon of a Simulator of the Human Intestinal Microbial Ecosystem (SHIME) reactor. The adhesion module consisted of a luminal chamber containing the growth medium and the inoculated bacterial strain and a basal chamber from which oxygen could diffuse across a semi-permeable polycarbonate membrane, which was covered on its luminal side with a mucin layer, relevant for the specific region of the gastrointestinal tract. The contact time between the inoculated bacteria and the functional layer was established in 1.5 h. Next, the luminal suspension was removed and the non-adhered bacteria were removed from the mucus layer by rinsing the functional layer twice with PBS. Subsequently, the luminal side of the functional layer was rinsed with Triton X-100 to remove the adhered bacteria. The obtained suspension was analyzed for microbial concentration using plate counts specific for different bacterial groups. *Lactobacillus rhamnosus* GG adhered strongly to the mucin-agar layer, with the percentage adhesion (15.7±3.2%) being a factor 6.19 higher than for adhesion to mucin-free agar. Regarding the complex microbial community of the SHIME reactor, adhesion differed substantially between bacteria and decreased from total Lactobacilli (27.0±4.1%) over faecal coliforms (18.3±3.6%), total Bifidobacteria (12.9±1.5%) and total Clostridia (1.8±0.3%) to total anaerobes (0.6±0.1%). Although not further analyzed at this moment, also the medium and optionally present cells of the basal chamber can be sampled and analyses can be conducted to estimate the simulated host's cellular response.

6. Cell Line Survival

An adhesion module was assembled with two chambers separated by a semi-permeable membrane (i.e. polycarbonate, pore size: 0.4 µm) on which the mucus layer was poured. The top compartment was inoculated with a bacterial community from the ascending colon of an in vitro dynamic simulator of the GI tract. In the bottom compartment a pure monolayer of Caco-2 cells was allowed to grow. The module allowed the indirect and continuous interaction between the growing biofilm and the enterocyte monolayer. The semi-permeable membrane between the two chambers allowed the exchange of signalling molecules between the biofilm and the epithelium cells as well as the $O_2$ diffusion to the bottom of the microbial biofilm.

In a second setup, the direct contact between the GIT-derived microbial community and the cell line was allowed. Cell viability between both set-ups was compared by means of the MTT ((3-(4,5-Dimethylthiazol-2-yl)-2,5-diphenyltetrazolium bromide) colorimetric test after 48 h of incubation for the first setup and after 2 h in the second setup. To evaluate possible cytotoxicity phenomena in the enterocyte chamber, different settings (in triplicate) have been tested: a) addition of a non-diluted bacterial suspension; b) application of a 1:4 diluted bacterial suspension. These two conditions in combination with: 1) semi-continuous flow of fresh medium every 24 h; 2) semi-continuous flow of fresh medium every 5 h. As a negative control a filter-sterilized suspension of the bacterial inoculum was re-circulated in the upper compartment.

As shown in FIG. 1, in the tested conditions the cell viability after 48 h of incubation was not significantly different from the control while, by direct contact, the viability dramatically decreased already after 2 h. The morphology of the cells was also evaluated by phase-contrast microscopy comparing the control with the treated cells after 48 h of incubation, however, there was no difference between the controls and treated cells (data not shown).

7. Adhesion Potential of Mixed Microbial Communities in Response to a Prebiotic Short-Term Treatment A second objective of working with the in vitro adhesion module is to explore the adhesion potential of selected microbial cultures in the presence of a complex microbial community relevant for the terminal ileum and colon respectively and to evaluate the host cellular response towards this community. To this end, a suspension of the ascending colon compartment of a SHIME system was sampled and inoculated in the luminal chamber of the adhesion module in presence of inulin with a degree of polymerization between 2 and 20, and arabinoxylans (AX) with a degree of substitution of 0.7, and a strongly varying degree of polymerization (on average 200). The short-term effect of these functional foods was evaluated. AX decreased the adhesion capacity of all the investigated groups, whereas inulin had less or no influence (data not shown).

8. Measuring the Bioavailability of Prokaryotic and Eukaryotic Metabolites

The experimental setup of the adhesion module which incorporates a semi-permeable membrane besides the mucus layer allows not only the diffusion of oxygen from the basal to the luminal side, but also the transport of specific compounds of interest from the luminal to the basal side. In principle, measuring these compounds of interest in the basal suspension would give an estimation of the bioavailability of those compounds. In this study, we characterize the prokaryotic and eukaryotic metabolites in the serosal suspension by means of GC-MS technique 24 h after the inoculation of the device with a bacterial suspension originating from the ascending colon of a SHIME system (luminal side) and with Caco-2 cells (lower chamber). The presence and absence of bacteria in the luminal compartment induced a clearly different metabolic profile in the serosal compartment (data not shown).

9. In Vitro Evaluation Over Long Timeframe of Prebiotics Compounds on the Microbial Community Associated to the Human Gut Wall The aim of this study was to evaluate the effect of known prebiotic compounds (inulin and arabinoxylan—AX) on the microbiota associated with the gut wall in different areas of the GI tract and under long-term representative conditions. For this purpose, the adhesion module was used together with a well-validated gastrointestinal model—the Simulator of the Human Intestinal Microbial Ecosystem (SHIME). Clearly, the inherent adhesion potency, the specific growth rate, the state of mucus layer and interaction with endogenous microorganisms (adhered or in suspension) determined the microbial potency to colonize the intestinal epithelium.

9.1 The SHIME

The reactor setup is adapted from the system, representing the gastrointestinal tract of the adult human, as described by Molly et al. (1993). The SHIME consists of a succession of five reactors simulating the different parts of the human gastrointestinal tract. The first two reactors are of the fill-and-draw principle to simulate different steps in food uptake and digestion, with peristaltic pumps adding a defined amount of SHIME feed (140 mL 3×/day) and pancreatic and bile liquid (60 mL 3×/day), respectively to the stomach (V1) and duodenum (V2) compartment and emptying the respective reactors after specified intervals. The last three compartments are continuously stirred reactors with constant volume and pH control. Retention time and pH of the different vessels are chosen in order to resemble in vivo conditions in the different parts of the gastrointestinal tract. The overall residence time of the last three vessels, simulating the large intestine, is 76 h. Upon inoculation with fecal microbiota, these reactors simulate the ascending (V3), transverse (V4) and descending (V5) colon. Inoculum preparation, retention time, pH, temperature settings and reactor feed composition were previously described by Possemiers et al. (2004). In the TWINSHIME, two systems with identical environmental conditions (identical pH and temperature control) are run in parallel. The investigative capacities of the SHIME are then expanded with the connection of two biofilm adhesion modules in parallel to each small intestine compartment. Finally, 21 oxygen-releasing beads covered with a mucus layer are added to each of the colon compartments.

9.2. Experiment Design for the SHIME:

Stabilization Period:

The colon compartments of the SHIME reactors are first inoculated with an isolated fecal microbial community of a selected healthy volunteer. The SHIME reactor is operated under nominal conditions to stabilize the microbial community and to let it adapt its metabolic activity and community composition to the conditions prevailing in the respective colon compartments. This stabilization period lasts for 3 weeks.

Basal Period:

During the basal period, the SHIME reactor is operated under nominal conditions. Parameters such as short chain fatty acid (SCFA) production and ammonium production are determined 3 times/week and plate count analyses are performed once a week for selected bacterial groups (total (an) aerobes, total Clostridia, lactobacilli, bifidobacteria, total coliforms, staphylococci). The results of these analyses serve as the background values to be used to compare the measured parameters from the treatment period. The adhesion modules are connected to the small intestine vessels and the beads are added to the colon vessels. The basal period lasts 2 weeks.

Treatment Period:

During the treatment period, the SHIME reactor is operated under nominal conditions, but with a modified diet containing a lower amount of starch in the medium compared to that of the basal period and the effect of a specific compound (inulin or arabinoxylan—2.5 g/L) is tested. SCFA and ammonium production are determined 3 times/week and plate count analysis is performed once a week. This treatment period typically lasts for 3 weeks.

Washout Period:

During the washout period, the SHIME reactor is operated under nominal conditions, with the initial diet. SCFA and ammonium production are determined 3 times/week and plate count analysis is performed once a week. Analysis of these microbial parameters allows to assess whether possible changes from the treatment period normalize again to the levels of the basal period.

9.3 Results on Biofilm Formation:

Each adhesion module was connected in parallel with the ascending colon reactors and was substituted with a new one every 24 h (maximal exposure per membrane=48 h). The ascending colon content was allowed to circulate on the functional layer with a flow rate of 10 mL/min. The effect of the tested products was evaluated by means of the so-called Adhesion Related Prebiotic Index (AR-PI) for the mucin-adhered microbial community. Plate counts (performed before and after the treatment) on specific media for Lactobacilli, bifidobacteria, clostridia, fecal coliforms and total anaerobes indicated that inulin and AX (arabinoxylan) exerted a prebiotic effect on the mucin-adhered microbiota of the SHIME (AR-PI of 14 and 70, respectively). AX was particularly potent in stimulating the adhered lactobacilli. Denaturant Gradient Gel Electrophoresis (DGGE) specific for bifidobacteria showed that different species dominated this microbial group in the luminal or the adhered fraction. Overall, the effect of AX on the luminal and mucin-associated bacteria was stronger and more permanent compared to that of inulin.

10. Biofilm Formation in the Oral Mucosa Model

Figure 6:
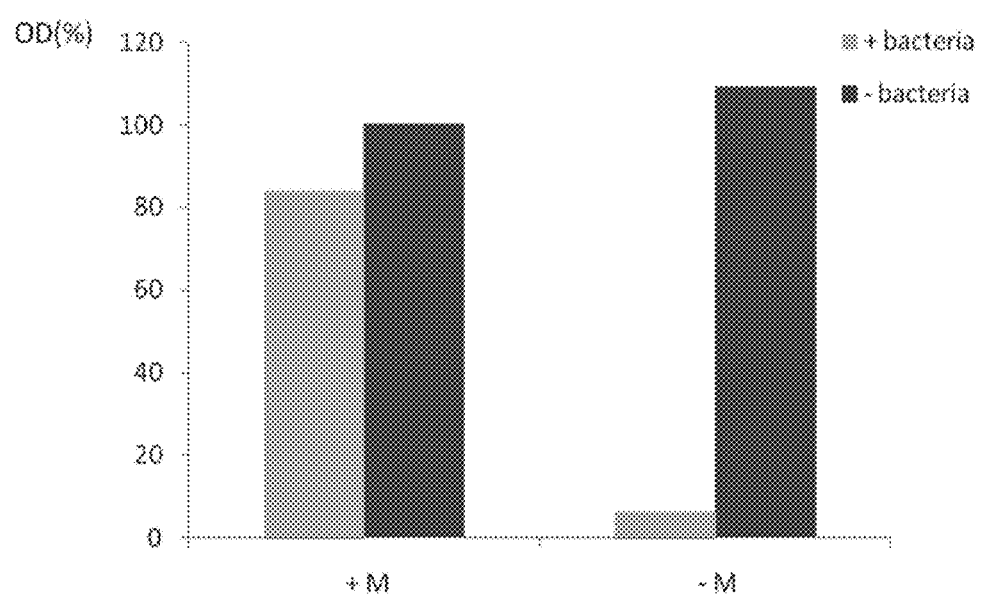
FIG. 6: Effect of the presence (+M) or absence (−M) of the mucus layer on the viability of oral TR146 cells after 55 hours of treatment in presence or absence of oral bacteria.

An adhesion module was assembled with two chambers separated by a semi-permeable membrane (i.e. polycarbonate, pore size: 0.4 µm) on top of which the mucus layer was poured and the oral biofilm was allowed to grow. The top compartment was inoculated with a bacterial suspension obtained form a mouth swab from the inner cheek. In the bottom compartment a monolayer of oral epithelial TR146 cells was allowed to grow. The module allowed the indirect and continuous interaction between the growing biofilm and the epithelial monolayer. The semi-permeable membrane between the two chambers allowed the exchange of signalling molecules between the biofilm and the epithelium cells as well as the $O_2$ diffusion to the bottom of the microbial biofilm. Viability of the TR146 monolayer was evaluated in presence or absence of the oral biofilm by means of the MTT ((3-(4,5-Dimethylthiazol-2-yl)-2,5-diphenyltetrazolium bromide) colorimetric test. FIG. 6 shows that the presence of the mucin layer is critical for the long-term survival (55 hours of treatment) of the oral epithelium in presence of the oral biofilm.

REFERENCES

Atuma C., Strugala V., Allen A., and Holm L. (2001) The adherent gastrointestinal mucus gel layer: thickness and physical state in vivo. *Am. J. Physiol. Gastrointest. Liver Physiol.* 280: G922-G929

Cani P. and Delzenne N. (2007) Gut microflora as a target for energy and metabolic homeostasis. *Curr. Opin. Clin. Nutr. Metab.* 10(6): 729-734

Cheesman and Guillemin (2007) We know you are in there: conversing with the indigenous gut microbiota. *Res. Microb.* 158: 2-9

Costerton J. W. (1995) Overview of microbial biofilms. *J. Ind. Microbiology and Biotechnology* 15: 137-140

Hooper and Gordon (2001) Commensal Host-Bacterial Relationship in the Gut. *Science* 292: 1115-1118

Hori Y, Nishida K, Yamato M, Sugiyama H, Soma T, Inoue T, Maeda N, Okano T, Tan θY. (2008) Differential expression of MUC16 in human oral mucosal epithelium and cultivated epithelial sheets. *Exp Eye Res*. September 87(3): 191-6.

Hori Y., H. Sugiyama, T. Soma and K. Nishida (2007) Expression of membrane-associated mucins in cultivated human oral mucosal epithelial cells. *Cornea* 26: S65-S69

Huycke and Moore (2002) In vivo production of hydroxyl radical by *enterococcus faecalis* colonizing the intestinal tract using aromatic hydroxylation. *Free Radicals in Biology and Medicine* 33: 818-826.

Kolenbrander, P. E., R. N. Andersen, K. M. Kazmerzak, and J. R. J. Palmer. (2000) Coaggregation and coadhesion in oral biofilms, p. 65-85. In D. G. Allison, P. Gilbert, H. M. Lappin-Scott, and M. Wilson (ed.), Community structure and co-operation in biofilms. Cambridge University Press, Cambridge, United Kingdom.

Laube, B., Winkler, S., Ladstetter, B., Scheller, T., and Schwarz, L. R. (2000). Establishment of a novel in vitro system for studying the interaction of xenobiotic metabolism of liver and intestinal microflora. *Arch Toxicol* 74, 379-387.

Lebeer, S., De Keersmaecker, S. C. J., Verhoeven, T. L. A., Fadda, A. A., Marchal, K., and Vanderleyden, J. (2007) Functional analysis of luxS in the probiotic strain *Lactobacillus rhamnosus* GG reveals a central metabolic role important for growth and biofilm formation. J Bact. 189: 860-871.

Lindén, S. K., Driessen, K. M., and McGuckin, M. A. (2007) Improved in vitro model systems for gastrointestinal infection by choice of cell line, pH, microaerobic conditions, and optimization of culture conditions. *Helicobacter.* 12: 341-53.

Liu B., J. R. Lague, D. P. Nunes, P. Toselli, F. G. Oppenheim, R. V. Soares, R. F. Troxler and G. D. Offner (2002) Expression of membrane-associated mucins MUC1 and MUC4 in major human salivary glands. J. Histochem. *Cytochem.* 50: 811-820.

Macfarlane and Dillon, (2007) Microbial biofilms in the human gastrointestinal tract. *J Appl Microbiol.* 102: 1187-1196

Macfarlane and Macfarlane (2007) Models for intestinal fermentation: association between food components, delivery systems, bioavailability and functional interactions in the gut. *Curr Opin Biotechnol.* 18: 156-162

Macfarlane S, Woodsmansey E and Macfarlane G. (2005) Colonization of mucin by human intestinal bacteria and establishment of biofilm communities in a two-stage continuous culture system. *Appl. Environ. Microbiol.* 71: 7483-7492

Mäkivuokko H A, Saarinen M T, Ouwehand A C, Rautonen N E. (2006) Effects of lactose on colon microbial community structure and function in a four-stage semicontinuous culture system. *Biosci. Biotechnol. Biochem.* 70 (9): 2056-63

Minekus M., Smeets-Peeters M., Bernalier A., Marol-Bonnin S., Havenaar R., Marteau P., Alric M., Fonty G. and Huis in't Veld J. H. J. (1999) computer-controlled system to simulate conditions of the large intestine with peristaltic mixing, water absorption and absorption of fermentation products. *Appl. Microb. Biotech.* 53: 108-114

Molly K., Woestyne M. V. and Verstraete W. (1993) Development of A 5-Step Multichamber Reactor As A Simulation of the Human Intestinal Microbial Ecosystem. *Applied Microbiology and Biotechnology* 39, 254-258

Nielsen P. A., E. P. Bennett, H. H. Wandall, M. H. Therkildsen, J. Hannibal and H. Clausen (1997) Identification of a major human high molecular weight salivary mucin (MG1) as tracheobronchial mucin MUC5B. *Glycobiology* 7: 413-419.

Nollevaux G., Devillé C, El Moualij B., Zorzi W., Deloyer P., Schneider Y., Peulen O. and Dandrifosse G. (2006) Development of a serum-free co-culture of human intestinal epithelium cell-lines (Caco-2/HT29-5M21). *BMC Cell Biol.* 7:20

Parlesak A., Haller D., Brinz S., Baeuerlein A., Bode C. (2004) Modulation of Cytokine Release by Differentiated CACO-2 Cells in a Compartmentalized Coculture Model with Mononuclear Leucocytes and Nonpathogenic Bacteria. *Scandinavian Journal of Immunology* 60, 477-485

Pedersen and Tannock (1989) Colonization of the porcine gastrointestinal tract by lactobacilli. *Appl Environ Microbiol.* 55(2): 279-283

Possemiers S., Verthe K., Uyttendaele S., Verstraete W. (2004) PCR-DGGE-based quantification of stability of the microbial community in a simulator of the human intestinal microbial ecosystem. *FEMS Microbiology Ecology,* 49: 495-507

Probert and Gibson (2004) Development of a fermentation system to model sessile bacterial populations in the human colon. *Biofilms* 1: 13-19

Sengupta A., D. Valdramidou, S. Huntley, S. J. Hicks, S. D. Carrington and A. P. Corfield (2001) Distribution of MUC1 in the normal human oral cavity is localized to the ducts of minor salivary glands. *Arch. Oral Biol.* 46: 529-538

Straub, T. M., K. Höner zu Bentrup, P. Orosz-Coghlan, A. Dohnalkova, B. K. Mayer, R. A. Bartholomew, C. O. Valdez, C. J. Bruckner-Lea, C. P. Gerba, M. Abbaszadegan, and C. A. Nickerson. (2007) In vitro cell culture infectivity assay for human noroviruses. *Emerging Infectious Diseases.* 13:396-403.

What is claimed is:

1. A method for co-culturing viable cells and growing microorganisms comprising:
providing an adhesion module comprising a basal compartment and a luminal compartment separated by a semi-permeable membrane; said membrane having an artificial mucus layer applied on its luminal side; wherein said module exhibits anaerobic conditions at its luminal side and aerobic conditions at its basal side; wherein the basal compartment of the module comprises viable cells; and wherein one or more growing microorganisms are attached to said artificial mucus layer; and
applying a continuous or semi-continuous flow of fresh growth medium to the luminal compartment creating shear forces applied to the surface of the mucus layer which allows co-culturing of said viable cells and growing microorganisms for at least 48 hours; wherein the flow into said luminal chamber is in a counter current direction from the flow into said basal chamber.

2. The method of claim 1 wherein the mucus layer comprises at least one mucin and the thickness of the layer is between 1-1000 µm.

3. The method of claim 1 wherein the aerobic conditions in the basal compartment of the module results in a partial oxygen pressure at the basal side of the mucus layer of between about 1 and 150 mmHg.

4. The method of claim 1, wherein the semi-permeable membrane allows the transport of components between 1-100000 Da.

5. The method of claim 1, wherein the material of the semi-permeable membrane is selected from the group consisting of polycarbonate, poly(diallyldimethylammonium chloride), polyethylene terephtalate, or polyamide (nylon).

6. The method of claim 1 wherein said basal side of said semi-permeable membrane further comprises a supportive porous layer.

7. The method of claim 6 wherein said supportive porous layer is selected from the group consisting of poly(diallyldimethylammonium chloride), poly(acrylic acid) or combinations thereof.

8. The method of claim 1 wherein the viable cells comprise Caco-2 cells and/or HT29 cells.

9. The method of claim 1 wherein the viable cells grow in a monolayer with their apical side towards the semi-permeable membrane.

10. The method as claimed in claim 1 wherein the surface area of the artificial mucus layer is between about 1 $cm^2$ and 1000 $cm^2$.

11. The method of claim 1 wherein said viable cells comprise enterocytes.

* * * * *

UNITED STATES PATENT AND TRADEMARK OFFICE
CERTIFICATE OF CORRECTION

PATENT NO. : 8,703,479 B2
APPLICATION NO. : 13/861590
DATED : April 22, 2014
INVENTOR(S) : Massimo Marzorati et al.

It is certified that error appears in the above-identified patent and that said Letters Patent is hereby corrected as shown below:

In the Specification:

Col. 2, Line 25,
"MKN7 and MNK45 cell-lines (Linden et al., 2007), it is not" should read
--MKN7 and MKN45 cell-lines (Linden et al., 2007), it is not--;

Col. 3, Line 9,
"MUC15, and MUC17 (Hori et al., 2007; Hon et al., 2008)." should read
--MUC15, and MUC17 (Hori et al., 2007; Horl et al., 2008).--;

Col. 4, Line 19,
"species such as for example $O_2^-$, $H_2O_2$ and OH from bac-" should read
--species such as for example $O_2^{\circ-}$, $H_2O_2$ and $OH^\circ$ from bac--;

Col. 6, Line 20,
"h for further analyses of on the biofilm" should read
--h for further analyses of the biofilm--;

Col. 9, Line 35,
"cells are grow in a monolayer with their apical side towards" should read
-- cells are grown in a monolayer with their apical side towards--;

Col. 10, Line 52,
"Strict anaerobes grow only were oxygen is absent. Some" should read
-- Strict anaerobes grow only where oxygen is absent. Some--;

Col. 11, Line 6,
"Cytophagarequire oxygen but grow best just below the" should read
--Cytophaga require oxygen but grow best just below the--;

Signed and Sealed this
Fifteenth Day of September, 2015

Michelle K. Lee
*Director of the United States Patent and Trademark Office*

CERTIFICATE OF CORRECTION (continued)
U.S. Pat. No. 8,703,479 B2

Col. 12, Line 4,
"*muc5, much, muc7, muc8* and *muc9* and their relative sub-" should read
--*muc5, muc6, muc7, muc8* and *muc9* and their relative sub- --;

Col. 13, Line 14,
"are 15-20 dyne/cm$^2$ with a residence time of 1 hour when" should read
--are 15-20 dynes/cm$^2$ with a residence time of 1 hour when--;

Col. 13, Line 16,
"are 8-12 dyne/cm$^2$ with a residence time of 2 hour when" should read
--are 8-12 dynes/cm$^2$ with a residence time of 2 hours when--;

Col. 13, Line 18,
"are 4-6 dyne/cm$^2$ with a residence time of 10 hour when" should read
--are 4-6 dynes/cm$^2$ with a residence time of 10 hours when--;

Col. 13, Line 20,
"are 2-3 dyne/cm$^2$ with a residence time of 24 hour when" should read
--are 2-3 dynes/cm$^2$ with a residence time of 24 hours when--;

Col. 13, Lines 22-23,
"are 0.5-3 dyne/cm$^2$ when simulating the respiratory tract at rest breathing (it can reach 1700 dyne/cm$^2$ with cough" should read
--are 0.5-3 dynes/cm$^2$ when simulating the respiratory tract at rest breathing (it can reach 1700 dynes/cm$^2$ with cough--;

Col. 13, Line 66,
"grow with there apical side towards the functional layer or" should read
--grow with their apical side towards the functional layer or--;

Col. 20, Lines 45, 46 and 47,
"resulted to be 4.9.10$^{-4}$ cm/sec with a relative diffusion coefficient ($D_{O2}$) of 9.8·10$^{-6}$ cm$^2$/sec; and for polyamide $Pm_{O2}$= 2.5 - 10$^{-4}$ cm/sec, $D_{O2}$ = 5.0 - 10$^{-6}$ cm$^2$/sec."; should read
--resulted to be 4.9·10$^{-4}$ cm/sec with a relative diffusion coefficient ($D_{O2}$) of 9.8·10$^{-6}$ cm$^2$/sec; and for polyamide, $Pm_{O2}$= 2.5 · 10$^{-4}$ cm/sec, $D_{O2}$ = 5.0 · 10$^{-6}$ cm$^2$/sec.--;

Col. 23, Line 63,
"obtained form a mouth swab from the inner cheek. In the" should read
--obtained from a mouth swab from the inner cheek. In the--.

Col. 24, Line 29,
"Maeda N, Okano T, Tan Θ Y. (2008) Differential expression" should read
--Maeda N, Okano T, Tano Y. (2008) Differential expression--;